United States Patent
Gulliver et al.

(10) Patent No.: US 11,793,964 B2
(45) Date of Patent: Oct. 24, 2023

(54) NASAL CANNULA WITH FLOW RESTRICTOR

(71) Applicant: Fisher & Paykel Healthcare Limited, Auckland (NZ)

(72) Inventors: Laurence Gulliver, Auckland (NZ); Mark Thomas O'Connor, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 16/922,429

(22) Filed: Jul. 7, 2020

(65) Prior Publication Data

US 2020/0338293 A1 Oct. 29, 2020

Related U.S. Application Data

(63) Continuation of application No. 15/021,849, filed as application No. PCT/NZ2014/000204 on Sep. 19, 2014, now Pat. No. 10,709,861.

(60) Provisional application No. 61/880,433, filed on Sep. 20, 2013.

(51) Int. Cl.
*A61M 16/06* (2006.01)

(52) U.S. Cl.
CPC ........ *A61M 16/0666* (2013.01); *A61M 16/06* (2013.01); *A61M 16/0672* (2014.02); *A61M 16/0677* (2014.02); *A61M 16/0683* (2013.01); *A61M 16/0688* (2014.02); *A61M 2205/42* (2013.01); *A61M 2206/10* (2013.01); *A61M 2206/14* (2013.01); *A61M 2206/20* (2013.01)

(58) Field of Classification Search
CPC .............. A61M 16/00; A61M 16/0461; A61M 16/0666; A61M 16/0672; A61M 16/0683; A61M 16/1005; A61M 16/1045; A61M 2016/0015; A61M 19/00; A61M 2202/0003; A61M 2202/0064; A61M 2202/0208; A61M 16/0677; A61M 16/06–0605; F17C 2221/011
USPC ...... 128/201.13, 21, 22, 25, 202.13, 203.12, 128/13, 15–18, 204.12, 26, 207.18, 128/200.21, 204.24, 204.25; 604/6, 16
See application file for complete search history.

(56) References Cited

U.S. PATENT DOCUMENTS

| | | | |
|---|---|---|---|
| 1,125,542 A | 1/1915 | Humphries | |
| 4,422,456 A * | 12/1983 | Tiep ................. | A61M 16/0666 128/207.18 |
| 5,740,799 A | 4/1998 | Nielsen | |
| 6,679,265 B2 | 1/2004 | Strickland et al. | |
| 7,000,613 B2 | 2/2006 | Wood et al. | |

(Continued)

OTHER PUBLICATIONS

International Search Report; PCT/NZ2014/000204; dated Nov. 7, 2014; 5 pages.

*Primary Examiner* — Justine R Yu
*Assistant Examiner* — Alexander Morales
(74) *Attorney, Agent, or Firm* — Knobbe, Martens, Olson & Bear, LLP

(57) ABSTRACT

Nasal cannulas for providing respiratory therapy to patients can have a body, two prongs extending from the body, and a gases inlet on one side of the body. There can be a throttle or internal localized reduction in the cross-sectional area of a cavity defined by the internal walls of the cannula body in between the prongs. In at least some arrangements, the throttle can partially or substantially fully equalize flow between the prongs of the cannula.

20 Claims, 3 Drawing Sheets

(56) References Cited

U.S. PATENT DOCUMENTS

| | | | |
|---|---|---|---|
| 8,375,946 B2* | 2/2013 | Boussignac | A61M 16/0486 128/205.24 |
| 8,939,933 B2 | 1/2015 | Santora et al. | |
| 9,827,392 B2* | 11/2017 | Lei | A61M 16/01 |
| 10,046,133 B2 | 8/2018 | Kapust et al. | |
| 10,709,861 B2 | 7/2020 | Gulliver et al. | |
| 2004/0261797 A1 | 12/2004 | White et al. | |
| 2006/0137690 A1 | 6/2006 | Gunaratnam et al. | |
| 2006/0266361 A1 | 11/2006 | Hernandez | |
| 2009/0183739 A1 | 7/2009 | Wondka | |
| 2010/0192957 A1 | 8/2010 | Hobson et al. | |
| 2011/0067704 A1 | 3/2011 | Kooij et al. | |
| 2011/0214676 A1* | 9/2011 | Allum | A61M 16/0051 128/207.18 |
| 2012/0065569 A1 | 3/2012 | Steegers et al. | |
| 2013/0081637 A1 | 4/2013 | Foley et al. | |
| 2014/0158127 A1 | 6/2014 | Boucher et al. | |

* cited by examiner

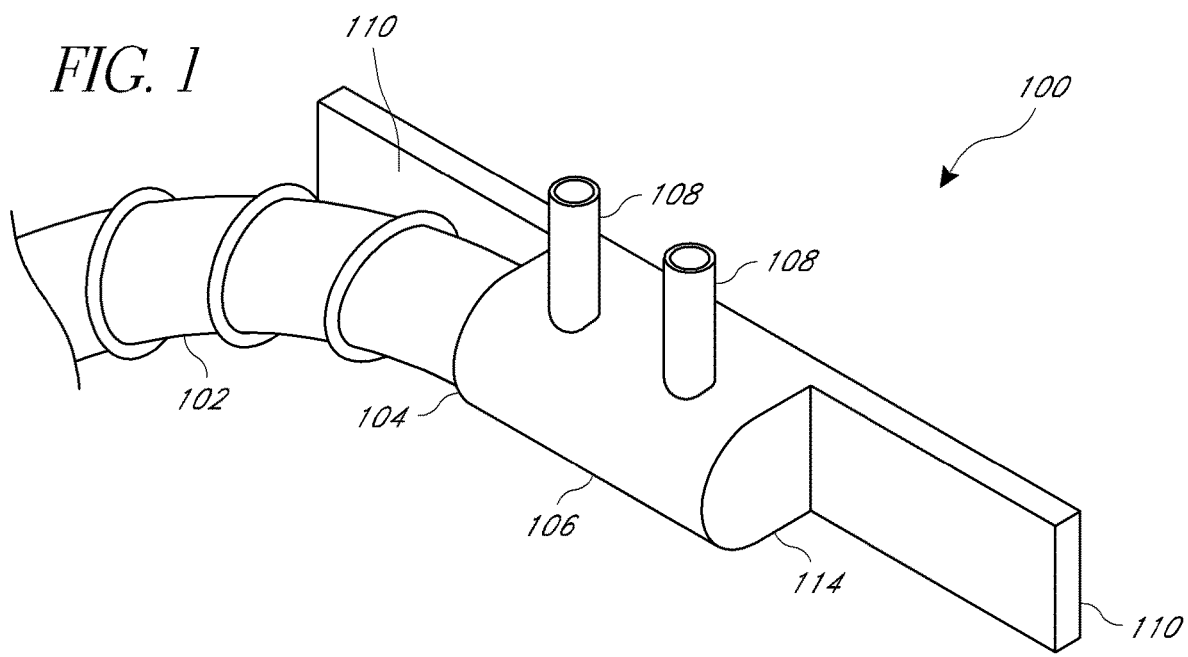
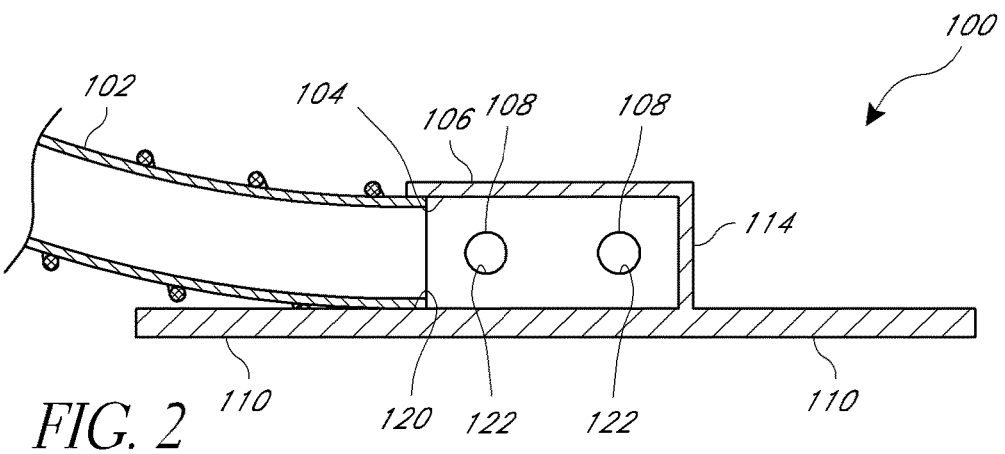
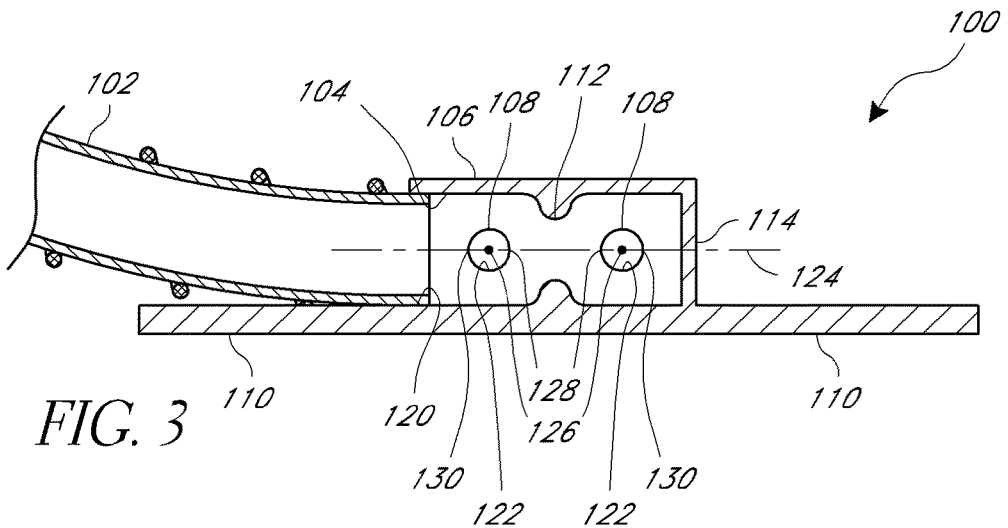

NASAL CANNULA WITH FLOW RESTRICTOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The present disclosure generally relates to systems and devices for providing gases to patients for respiratory therapy. More particularly, the present disclosure relates to nasal cannula interfaces for providing gases to patients via the nasal passages.

BACKGROUND OF THE INVENTION

Medical professionals may wish to provide patients with respiratory assistance in the form of supplemental oxygen or airflow for many reasons in ICU, other hospital, or home environments. Different types of interfaces for supplying gases to patients are available. For example, various nasal masks, full face masks, oral interfaces, nasal pillows, and nasal cannula interfaces exist. Nasal cannula interfaces can include two nasal prongs that are placed in the patient's nostrils to deliver gases to the patient.

SUMMARY OF THE INVENTION

In one or more configurations, the nasal cannula interfaces described herein can advantageously be used to deliver gases to patients over a wide range of concentrations and flow rates. In one or more configurations, the nasal cannula interfaces described herein also include various features designed to improve one or more of patient comfort, therapeutic benefit, efficiency, and/or provide other benefits.

In some configurations, a nasal cannula includes a central body portion defining a cavity. Two prongs extend from the central body portion. The central body portion also comprises an inlet adapted to receive gases from a gas source on only one side of the cannula. The central body portion comprises at least one localized reduction in cross-sectional area in the space of the cavity between the prongs.

In some configurations, an entirety of the localized reduction in cross-sectional area is located between inner edges of the openings of the prongs to the cavity.

In some configurations, the localized reduction in cross-sectional area extends beyond one or both of the inner edges of the openings of the prongs to the cavity.

In some configurations, an entirety of the localized reduction in cross-sectional area is located between outer edges of the openings of the prongs to the cavity.

In some configurations, the localized reduction in cross-sectional area is centered between the openings of the prongs to the cavity.

In some configurations, the localized reduction in cross-sectional area extends around an entire periphery of the cavity.

In some configurations, the localized reduction in cross-sectional area extends around only a portion of a periphery of the cavity.

In some configurations, the localized reduction in cross-sectional area is defined by a rounded projection of a wall of the body portion.

In some configurations, the localized reduction in cross-sectional area is defined by a squared projection of a wall of the body portion.

In some configurations, the localized reduction in cross-sectional area is defined by a triangular projection of a wall of the body portion.

In some configurations, the inlet is at a first end of the body portion and the body portion comprises a closed end wall at a second end.

In some configurations, the localized reduction in cross-sectional area is defined by an insert. In some configurations, the insert is a manifold that is coupled to a gases supply tube.

In some configurations, a nasal cannula comprises a central body portion defining a cavity. The nasal cannula further comprises a first prong and a second prong. Each of the first and second prongs extend from the central body portion. The first and second prongs define respective first and second passages that communicate with the cavity. The nasal cannula comprises an inlet to the cavity, wherein the inlet is adapted to allow a flow of gas from a gas source to enter the cavity. The flow of gas has a flow direction. A flow restrictor is within the cavity and is located between the first prong and the second prong along the flow direction.

In some configurations, an entirety of the flow restrictor is located between inner edges of the openings of the passages to the cavity.

In some configurations, the flow restrictor extends beyond one or both of the inner edges of the openings of the passages to the cavity.

In some configurations, an entirety of the flow restrictor is located between outer edges of the openings of the passages to the cavity.

In some configurations, the flow restrictor is centered between the openings of the passages to the cavity.

In some configurations, the flow restrictor extends around an entire periphery of the cavity.

In some configurations, the flow restrictor extends around only a portion of a periphery of the cavity.

In some configurations, the flow restrictor is defined by a rounded projection of a wall of the body portion.

In some configurations, the flow restrictor is defined by a squared projection of a wall of the body portion.

In some configurations, the flow restrictor is defined by a triangular projection of a wall of the body portion.

In some configurations, the inlet is at a first end of the body portion and the body portion comprises a closed end wall at a second end.

In some configurations, a nasal cannula comprises a central body portion defining a cavity. The central body portion comprises an inlet and a closed end. The inlet is adapted to receive gases from a gas source. A pair of prongs extends from the central body portion. The prongs are located between the inlet and the closed end. The nasal cannula comprises means for restricting a flow of gases within cavity between the prongs.

BRIEF DESCRIPTION OF THE DRAWINGS

Specific embodiments and modifications thereof will become apparent to those skilled in the art from the detailed description herein having reference to the figures that follow.

FIG. 1 is a perspective view of a nasal cannula system.

FIG. 2 is a top view of a cross-section of the nasal cannula system of FIG. 1.

FIG. 3 is a top view of a cross-section of a nasal cannula system with an internal annular ridge placed on the internal wall of the cannula body between the prongs.

DETAILED DESCRIPTION

Figure 4:
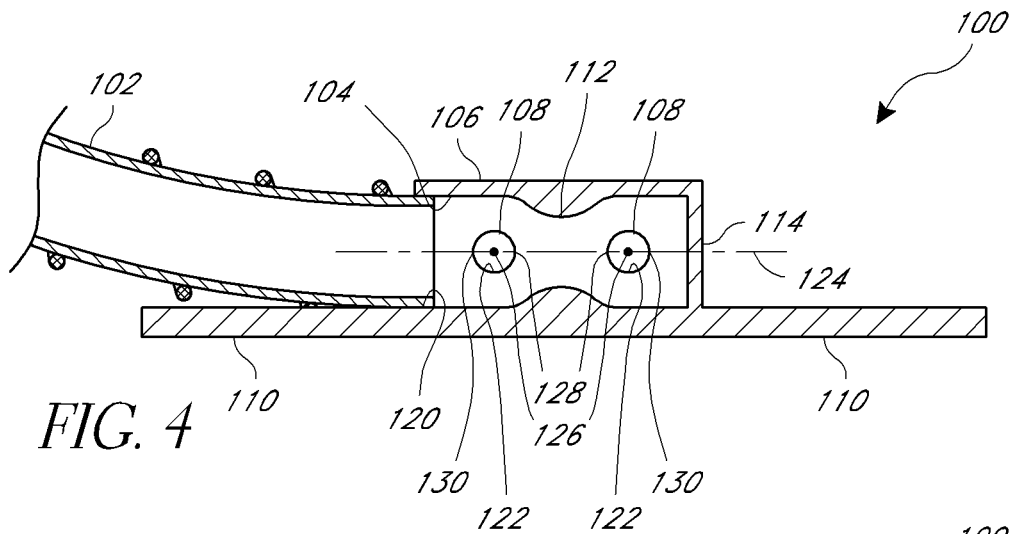
FIG. 4 is a top view of a cross-section of a nasal cannula system similar to that of FIG. 3, but with a more gradually sloping ridge.

With reference to FIGS. 1 and 2, a configuration of a nasal cannula system 100 is shown. In the illustrated configuration, the nasal cannula system 100 comprises a nasal cannula body 106 and a gases supply tubing 102. The gases supply tubing 102 is coupled to the nasal cannula body 106 to deliver a flow of breathing gas to a cavity 104 of the nasal cannula body 106. In the illustrated configuration, an inlet 120 to the cavity 104 is on one side of the body 106. In particular, the inlet 120 is on one end of the body 106 and opens to one end of the cavity 104. Thus, the gases supply tubing 102 provides the flow of breathing gas to one end of the cavity 104 and the flow of breathing gas moves along a flow direction from one end of the cavity 104 toward the other end of the cavity 104. In some configurations, the gases supply tubing 102 may be removable from the cavity 104. In some configurations, the cavity 104 may be open on two sides of the cannula body 106 and two gases supply tubes 102 (or a single supply tube 102 that is bifurcated into two delivery branches) may be used. In some configurations, the inlet 120 may be located inward of an end of the nasal cannula body 106.

The nasal cannula body 106 can also comprise one or more prongs 108 that may be inserted into the nares of a patient and/or lateral portions or flaps 110 that may help to support the cannula body 106 on the patient's face. The prongs 108 define internal passages 122 that extend along the length of the prongs 108 and communicate with the cavity 104 such that breathing gases introduced into the cavity 104 are delivered to the patient through the passages 122 of the prongs 108. Preferably, the flow direction of the flow of breathing gases is along a spacing direction of the prongs 108. That is, the flow of breathing gases passes one of the prongs 108 before passing the other prong 108.

The flaps 110 may be adapted to connect to headgear straps and/or other retention elements or arrangements (not shown) that may be placed on and/or around the patient's head in such a way that the cannula body 106 may be supported on the patient's face such that the prongs 108 may be placed into one or both of the nares of the patient. For example, the flaps 110 may comprise side release buckles that may interface with similar buckles on headgear straps. In some configurations, the flaps 110 need not be present, and the headgear straps and/or other elements may interface directly or indirectly with the gases supply tubing 102, the cannula body 106, and/or prongs 108. In some configurations, the cannula system 100 can be secured to the face of a patient by using, for example, adhesive pads.

In the illustrated configuration shown in FIGS. 1 and 2, in use, the nasal cannula main body 106 may rest on or around the upper lip of a patient. A flow of breathing gases generated by a blower or other flow generator (not shown) may pass through the gases supply tubing 102 and into the cavity 104 of the cannula body 106, where it moves through the passages 122 of the one or more prongs 108 and into the nares of a patient. However, one potential disadvantage of the illustrated configuration may relate to the flow dynamics of the system 100 in use. For example, in some cases, after flow enters the cannula body 106, some of the flow may impact against the internal wall 114 (e.g., end wall) of the cannula body 106 opposite the air entry side of the cavity 104 (e.g., inlet 120), which may create a region of raised pressure in the breathing gas flow near the wall 114 of the cannula body 106 relative to the other side of the cannula body 106. This raised gas pressure in the region of cavity 104 near this wall 114, in turn, may bring about an increased gas flow rate in this region, which may bring about an increased gas flow rate of gases moving through the prong 108 closest to the wall 114 relative to the prong 108 furthest from the wall 114. This uneven flow between prongs 108 of the cannula body 106 may, for example, create an uncomfortable sensation for the patient, and may encourage uneven and/or reduced efficiency or inadequate flushing of CO2 from the patient airways stemming from the nares. In some cases, other flow dynamics may contribute to or cause uneven flow rates within the prongs 108.

In some configurations, the cannula system 100 can be configured to address the above disadvantage by placing a throttle or localized reduction in the cross-sectional area of the cavity 104 in the cannula body 106 in between the prongs 108. Such a localized reduction may be integrally moulded or co-moulded with the nasal cannula body 106, for example. In some configurations, the localized reduction in cross-sectional area can be defined by an insert. For example, in some configurations, the cannula system 100 can comprise a manifold that is coupled to the gases supply tubing 102 and is receivable within the cannula body 106. The manifold can define portions of the cavity 104 or the manifold and the cannula body 106 can cooperate to define the cavity 104. The throttle or localized reduction in cross-sectional area can be defined or carried by the manifold. In some configurations, the cannula body 106 can be open at each end and the manifold and, thus, the gases supply tube 102 can be inserted into either end of the cannula body 106 to position the gases supply tube 102 on a desired side of the cannula body 106. The other end of the cannula body 106 can be closed by a suitable closure, such as an end cap, plug or end of the manifold. Examples of a switchable manifold are disclosed in Applicant's application no. PCT/NZ2014/000040, filed Mar. 14, 2014, entitled NASAL CANNULA ASSEMBLIES AND RELATED PARTS, the entirety of which is incorporated by reference herein. In configurations incorporating a manifold, the manifold can be considered as a portion of the cannula body, unless indicated otherwise. Thus, descriptions of throttles or other localized reductions in cross-sectional area with respect to the illustrated cannula body 106 can also apply to configurations in which a manifold is incorporated and in which the throttle or other localized reduction in cross-sectional area is defined or carried by the manifold. Other suitable methods or arrangements for providing the localized reduction in cross-sectional area could also be used.

FIG. 3 illustrates a configuration of the cannula system 100 that incorporates an arrangement of a throttle or localized reduction in cross-sectional area in between the prongs 108. The cannula system 100 of FIG. 3 can be substantially similar to the cannula system 100 of FIGS. 1 and 2. That is, the cannula system 100 of FIG. 3 can comprise a nasal cannula body 106 and a gases supply tubing 102. The gases supply tubing 102 can be coupled to the nasal cannula body 106 to deliver a flow of breathing gas to a cavity 104 of the nasal cannula body 106. In the illustrated configuration, an inlet 120 to the cavity 104 is on one side of the cannula body 106. Preferably, the inlet 120 is located on one end of the cannula body 106 and opens to one end of the cavity 104. As a result, the gases supply tubing 102 provides the flow of breathing gas to one end of the cavity 104 and the flow of breathing gas moves along a flow direction from one end of the cavity 104 toward the other end of the cavity 104. Preferably, the flow of breathing gas enters only one end of the cavity 104; however, in some configurations, the cavity 104 may be present on two sides of the cannula body 106 and two gases supply tubes 102 may be used. In some configurations, the inlet 120 may be located inward of an end of the nasal cannula body 106.

The nasal cannula body 106 can also comprise one or more prongs 108 that may be inserted into the nares of a patient and/or lateral portions or flaps 110 that may help to support the cannula body 106 on the patient's face. The prongs 108 define internal passages 122 that extend along the length of the prongs 108 and communicate with the cavity 104 such that breathing gases introduced into the cavity 104 are delivered to the patient through the passages 122 of the prongs 108. Preferably, the flow direction of the flow of breathing gases is along a spacing direction of the prongs 108. That is, the flow of breathing gases passes one of the prongs 108 before passing the other prong 108. Preferably, the inlet 120 is positioned outwardly of the prongs 108 such that the flow of breathing gases passes the closest prong 108 before passing the furthest prong 108.

The flaps 110 may be adapted to connect to headgear straps and/or other retention elements or arrangements (not shown) that may be placed on and/or around the patient's head in such a way that the cannula body 106 may be supported on the patient's face such that the prongs 108 may be placed into one or both of the nares of the patient. For example, the flaps 110 may comprise side release buckles that may interface with similar buckles on headgear straps. The flaps 110 can be flexible, semi-rigid or rigid. Alternatively, the flaps 110 and/or the cannula body 106 could be coupled to a rigid frame that provides additional support or stability. For example, a rigid frame could be overmolded or otherwise formed onto the flaps 110 and/or cannula body 106. In some configurations, the flaps 110 need not be present, and the headgear straps and/or other elements may interface directly or indirectly with the gases supply tubing 102, the cannula body 106, and/or prongs 108. In some configurations, the cannula system 100 can be secured to the face of a patient by using, for example, adhesive pads.

The cavity 104 can have any suitable size or shape for delivery of a flow of breathing gases to the prongs 108. For example, the cavity 104 can be generally columnar or cylindrical in shape. As used herein, cylindrical includes circular cross-sectional spaces, as well as elongated spaces having other cross-sectional shapes. Because a surface of the cannula body 106 typically rests against the upper lip of a patient or user, one side of the cavity 104 and/or cannula body 106 can be generally flat such that the cross-sectional shape is similar to the letter "D," for example. In addition, because the prongs 108 are typically placed in the patient's nares, the length of the cannula body 106 supporting the prongs 108 is typically longer than a width of a patient's nose. The cannula body 106 can be made available in different lengths and/or cross-sectional sizes to accommodate a variety of users.

In some configurations, the cavity 104 is generally linear in a length direction such that the cavity 104 defines a linear longitudinal axis 124. In other arrangements, the cavity 104 can be curved along its length. The flow direction of the flow of breathing gases can be generally in a direction coaxial with or parallel to the longitudinal axis 124, such as when the inlet 120 is positioned at one end of and centered relative to the cavity 104. In other configurations, the flow direction may change along the length of the cavity 104; however, preferably, the flow direction is generally aligned with the longitudinal axis 124 in the area containing and between the prongs 108.

Preferably, openings of the passages 122 of the prongs 108 to the cavity 104 are spaced from one another along the longitudinal axis 124. The passages 122 can have centers 126 that are positioned on the longitudinal axis 124 or that are spaced (equally or unequally) in a lateral direction from the longitudinal axis 124. The passages 122 can have inner edges 128 that are closest to one another and outer edges 130 that are furthest from one another. A distance along the longitudinal axis 124 between the inner edge 128 and outer edge 130 of each passage 122 can define a width of the passage 122. In some configurations, the passages 122 have a generally circular cross-sectional shape; however, other shapes can also be used. The passages 122 can vary in cross-sectional shape along their length.

In the illustrated configuration shown in FIG. 3, in use, the nasal cannula body 106 may rest on or around the upper lip of a patient. A flow of breathing gases generated by a blower or other flow generator (not shown) may pass through the gases supply tubing 102 and into the cavity 104 of the cannula body 106, where it moves through the passages 122 of the one or more prongs 108 and into the nares of a patient. Other features of the cannula system 100 can be similar to any of those disclosed in Applicant's application no. PCT/NZ2014/000040, filed Mar. 14, 2014, entitled NASAL CANNULA ASSEMBLIES AND RELATED PARTS, the entirety of which is incorporated by reference herein. As described above, the cannula system 100 of FIG. 3 can comprise an arrangement that facilitates a more even flow rate of the breathing gases through the prongs 108 relative to one another.

For example, as shown in the configuration illustrated in FIG. 3, the nasal cannula body 106 may comprise an annular ridge 112 on the internal surface of the side wall of the cannula body 106. At least a portion of the ridge 112 can be positioned between the prongs 108. As the flow of breathing gases moves into the cavity 104 of the cannula body 106, the movement of the flow moving past the ridge 112 is resisted relative to movement of the flow upstream of the ridge 112, and this flow resistance at the ridge 112 lowers the gas pressure and gas flow rate of gases downstream of the ridge 112. Given that the prong 108 closest to the wall 114 of the body 106 is downstream of the ridge 112, introducing a localized reduction in flow area between the prongs 108, such as the ridge 112, may partially or fully equalize the flow rates of gases between the prongs 108, which may reduce discomfort and/or undesirably low or inadequate CO2 flushing, possibly among other benefits. In some configurations, the presence of the ridge 112 can improve the equalization of the flow rate between the prongs 108 relative to the same or similar structure without the ridge 112.

As described, the ridge 112 can be annular in shape. That is, the ridge 112 can encircle or extend completely around the longitudinal axis 124 along the circumference or perimeter of the cavity 104. In other arrangements, the ridge 112 can extend only partially around the longitudinal axis 124. For example, the ridge 112 can extend substantially around the longitudinal axis 124 or less than three-quarters, one-half or one-quarter of the way around (e.g., the circumference of) the longitudinal axis 124.

The illustrated ridge 112 is generally semi-circular in cross-sectional shape. However, other suitable shapes can also be used. The width of the ridge 112 can also vary. In the illustrated arrangement, an entire width of the ridge 112, or distance along the longitudinal axis 124, is located between the inner edges 128 of the passages 122. In other arrangements, the entire width of the ridge 112 can be located between the centers 126 of the passages 122 or between the outer edges 130 of the passages 122. In some arrangements, the ridge 112 can extend beyond the outer edges 130 of the passages 122.

In the illustrated arrangement, the ridge 112 is centered relative to the passages 122 of the prongs 108 (e.g., relative to the centers 126) along the longitudinal axis 124. That is, a geometric center of a cross-section of the ridge 112 can be centered between passages 122. However, in other arrangements, the ridge 112 can be off-center relative to the prongs 108. In some configurations, the ridge 112 can be adjustable along the longitudinal axis 124 (e.g., arrangements in which the ridge 112 is positioned on an insert). The cross-sectional shape of the ridge 112 can be symmetrical or asymmetrical.

Many possible reductions in the cross-sectional area of cavity 104 in between the prongs 108 may be used. Some possible configurations are illustrated in the following drawings of alternative arrangements. In the following arrangements, the cannula system 100 can be the same as or substantially similar to the cannula system 100 of FIG. 3. The following cannula systems 100 are described primarily in the context of the differences relative to the system 100 of FIG. 3. Accordingly, features or components not described in detail can be assumed to be the same as or similar to the corresponding features or components of the system 100 of FIG. 3. In addition, modifications and alternatives described in relation to the system 100 of FIG. 3 can also apply to the following systems 100. Features and optional arrangements of the ridge 112 described with respect to FIG. 3 can also generally apply to other reductions in cross-sectional area described herein.

In the configuration illustrated in FIG. 4, similar to the configuration illustrated in FIG. 3, an annular ridge 112 is positioned along the internal surface of the wall of the cannula body 106. However, the rise and fall of the ridge 112 in FIG. 4 in a direction aligned with the longitudinal axis 124 is more gradual than that of FIG. 3. Advantageously, the ridge 112 of FIG. 4, because of the gradual change in thickness of the cannula body 106, creates less turbulent flow than the ridge 112 of FIG. 3, which may reduce the noise generated by flow through the body 106 in use.

Figure 5:
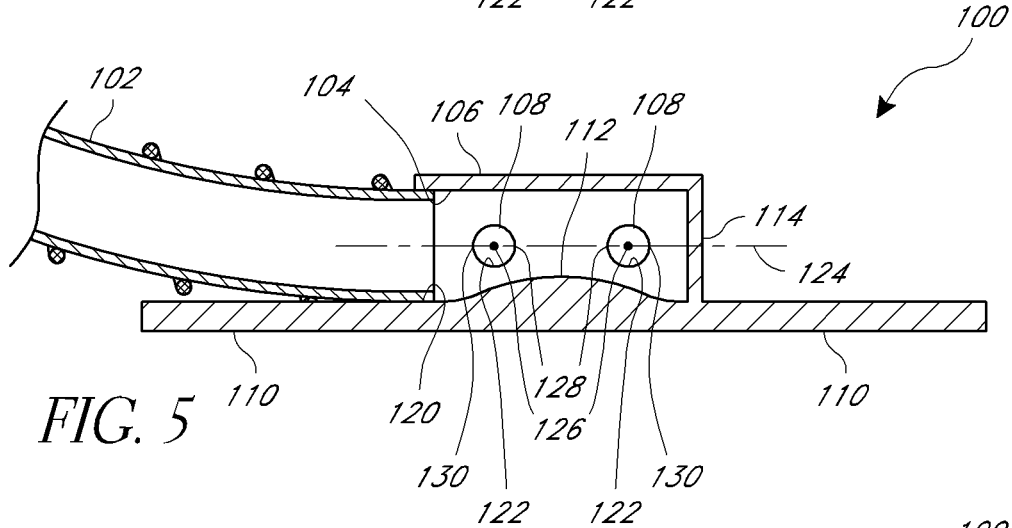
FIG. 5 is a top view of a cross-section of a nasal cannula system similar to that of FIG. 4, except the ridge slopes still more gradually and is not annular, but rather placed on a single side of the internal wall of the cannula body.

In the configuration illustrated in FIG. 5, similar to the configuration illustrated in FIG. 4, a ridge 112 is positioned along the internal surface of the wall of the cannula body 106. However, the rise and fall of the ridge 112 in FIG. 5 is still more gradual than that of FIG. 4. In some configurations, the ridge 112 can generally match the shape of the face of a user. Thus, the flaps 110 can be flexible or curved to follow a general curvature of the ridge 112 and, therefore, a curvature of a user's face. Additionally or in the alternative, the ridge 112 can be provided on only one side of the internal wall of the cannula body 106. The ridge 112 can be located opposite the prongs 108, can be located on the same side as the prongs 108 or can be located adjacent the prongs 108.

Figure 6:
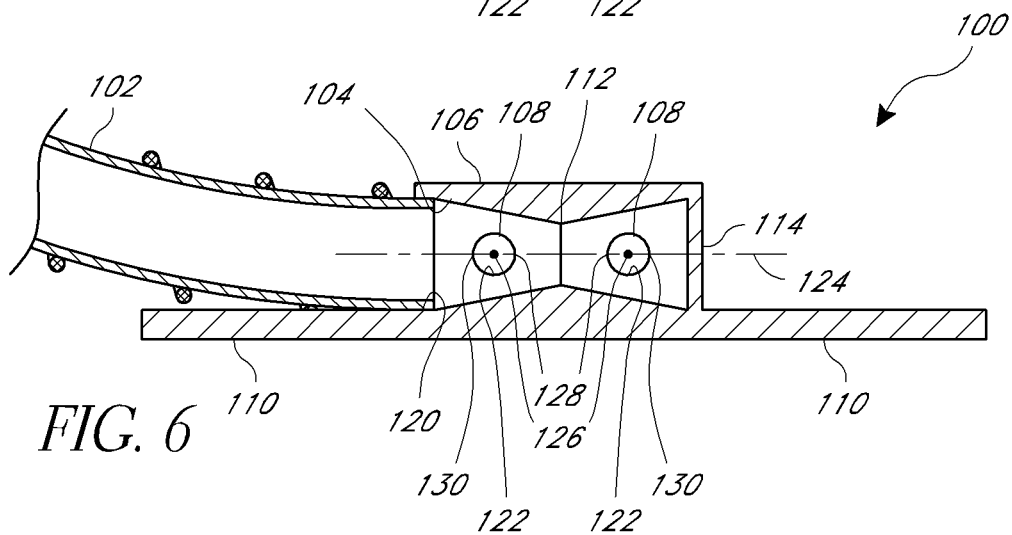
FIG. 6 is a top view of a cross-section of a nasal cannula system similar to that of FIG. 4, but with a taper towards a sharp middle point in the cannula body.

In the configuration illustrated in FIG. 6, similar to the configuration illustrated in FIG. 4, an annular ridge 112 is positioned along the internal surface of the wall of the body 106. However, the ridge 112 tapers towards a sharp edge at or near the middle of the internal wall of the cannula body 106 between the prongs 108 such that the ridge 112 defines a generally triangular cross-sectional shape. In other arrangements, the ridge 112 does not necessarily extend around an entire circumference or perimeter of the cavity 104.

Figure 7:
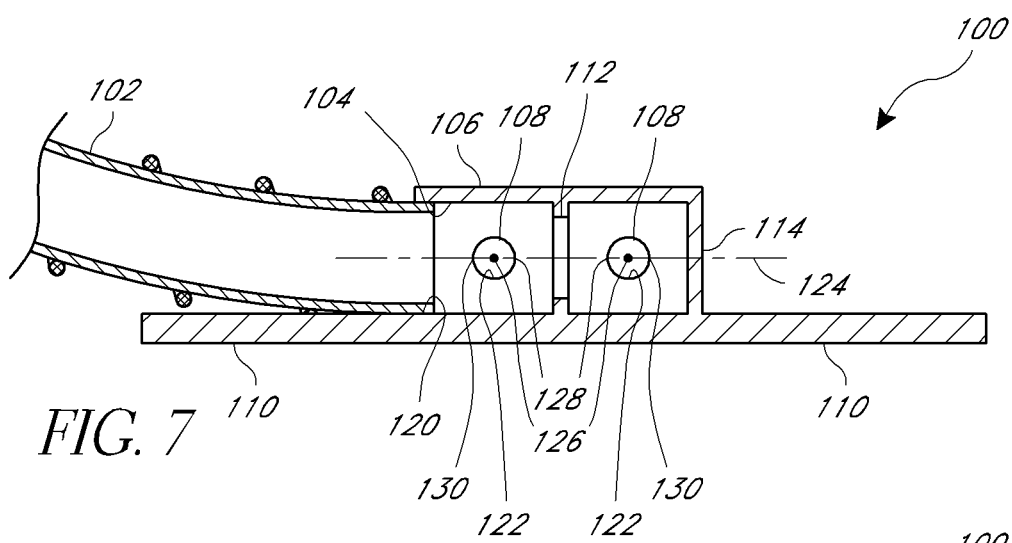
FIG. 7 is a top view of a cross-section of a nasal cannula system with an internal square or rectangular-shaped ridge placed on the internal wall of the cannula body between the prongs.

In the configuration illustrated in FIG. 7, similar to the configuration illustrated in FIG. 3, an annular ridge 112 is positioned along the internal surface of the wall of the cannula body 106. However, the ridge 112 in this configuration takes the form of a square or rectangular-shaped ridge 112 (in cross-section) instead of the (semi)circular or ellipsoidal shaped ridge 112 shown in the previous figures.

Figure 8:
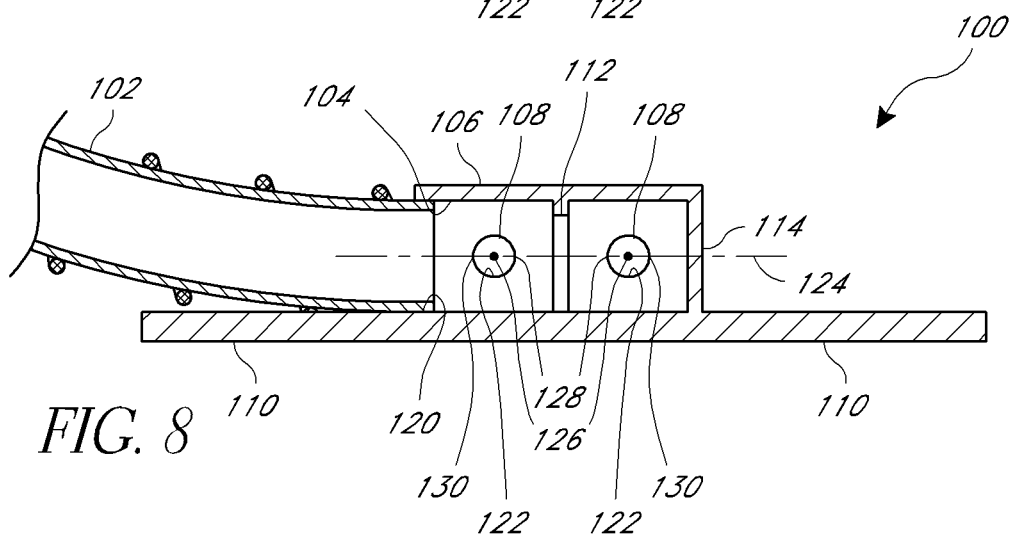
FIG. 8 is a top view of a cross-section of a nasal cannula system similar to that of FIG. 7, but with the internal ridge limited to a single side of the internal wall of the cannula body.

In the configuration illustrated in FIG. 8, similar to the configuration illustrated in FIG. 7, a ridge 112 is positioned along the internal surface of the wall of the cannula body 106. However, the ridge 112 does not extend around an entire circumference or perimeter of the cavity 104. In the illustrated configurations, the ridge 112 is limited to a single side of the internal wall of the body 106. In other arrangements, the ridge 112 can extend along a greater portion of the circumference or perimeter of the cavity 104 less than the entire circumference or perimeter.

Many other variations of configurations of internal ridges in the cannula body 106 may be used. For example, although the localized reduction of cross-sectional area as shown in the illustrated configurations takes the form of a single annular or localized ridge, the localized reduction may comprise any number of ridges of any thickness or gradient of slope. In some preferred configurations, the localized reduction is arranged so that it generates a relatively low level of turbulent flow and is easy to adapt to for injection mold tooling purposes. Additionally, the term 'ridge' as used in describing the illustrated configurations should not be taken as limiting, and any term that can convey an understanding of a localized reduction in cross-sectional area of the internal space of the cannula body 106, such as 'bump,' 'lump,' 'baffle,' 'rib,' or 'protrusion,' may be substituted. Moreover, any of the features described in connection with one particular ridge may be applied to other ridges.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Certain features, aspects and advantages of an embodiment of the present invention have been described with reference to nasal cannulas. However, certain features, aspects and advantages of the nasal cannulas as described above may be advantageously used with other therapeutic or non-therapeutic breathing interfaces, such as full face masks, nasal masks, oral masks, and nasal pillows. Certain features, aspects and advantages of the method and apparatus of the present disclosure may be equally applied to other breathing devices for other conditions.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

The invention claimed is:

1. A nasal cannula, comprising:
a central body portion comprising a cavity, a vertical flat interior surface and an inlet that allows a flow of gases from a gas source to enter the cavity, wherein two prongs extend from the central body portion,
at least one localized reduction in cross-sectional area comprising a ridge extending from the vertical flat interior surface, wherein a cross-sectional shape of the ridge is asymmetrical, the ridge being positioned between the two prongs such that an entirety of the at least one localized reduction in cross-sectional area is located between outer edges of openings into each of the two prongs, the at least one localized reduction in cross-sectional area changing the flow of gases downstream of the at least one localized reduction in cross-sectional area.

2. The nasal cannula of claim 1, wherein the ridge comprises a curved leading edge or a curved trailing edge.

3. The nasal cannula of claim 1, wherein the ridge comprises a tapered leading edge or a tapered trailing edge.

4. The nasal cannula of claim 1, wherein the ridge comprises one or more convergent or divergent sections.

5. The nasal cannula of claim 1, wherein the at least one localized reduction in cross-sectional area comprises at least one ridge.

6. The nasal cannula of claim 1, wherein the ridge is off-centered relative to the two prongs.

7. The nasal cannula of claim 1, wherein a manifold is received within the central body portion.

8. The nasal cannula of claim 1, wherein the manifold connects to either end of the central body portion.

9. The nasal cannula of claim 1, wherein a width of the ridge varies.

10. The nasal cannula of claim 1, wherein the flow of gases passes one of the two prongs and the ridge before passing the other of the two prongs.

11. The nasal cannula of claim 1, wherein a first central body portion cross-section is positioned upstream of the ridge and a second central body portion cross-section is positioned downstream of the ridge, each of the first and second central body portion cross-sections being greater than a cross-sectional area defined by the at least one localized reduction in cross-sectional area.

12. The nasal cannula of claim 1, wherein the at least one localized reduction in cross-sectional area changes the flow of gases downstream of the at least one localized reduction in cross-sectional area such that a downstream gas pressure that is downstream of the at least one localized reduction is lower than an upstream gas pressure that is upstream of the at least one localized reduction.

13. A nasal cannula, comprising:
a central body portion comprising a cavity, a vertical flat interior surface and an inlet that receives gases from a gas source, wherein a first prong and a second prong extend from the central body portion, the first prong being upstream relative to the second prong,
at least one localized reduction in cross-sectional area comprising a ridge extending from the vertical flat interior surface, the ridge being off-centered relative to the first prong and the second prong, the ridge being located entirely between the first prong and the second prong, and the at least one localized reduction in cross-sectional area changing a flow of gases downstream of the at least one localized reduction in cross-sectional area.

14. The nasal cannula of claim 13, wherein the ridge is positioned closer to the first prong, which is closest to the inlet, than the second prong.

15. The nasal cannula of claim 13, wherein the ridge is positioned closer to the second prong, which is farthest from the inlet, than the first prong.

16. The nasal cannula of claim 13, wherein a cross-sectional shape of the ridge comprises a rounded projection.

17. The nasal cannula of claim 13, wherein a cross-sectional shape of the ridge comprises a squared or triangular projection.

18. The nasal cannula of claim 13, wherein a cross-sectional shape of the ridge is asymmetrical.

19. The nasal cannula of claim 13, further comprising a manifold receivable within the central body portion.

20. A nasal cannula, comprising:
a central body portion comprising a cavity, a vertical flat interior surface and an inlet that allow a flow of gases from a gas source to enter the cavity, wherein a first prong and a second prong extend from the central body portion,
at least one localized reduction in cross-sectional area comprising a ridge extending from the vertical flat interior surface, the ridge comprising an asymmetric gradient of slope, the ridge being positioned fully between the first prong and the second prong, an apex of the ridge being closer to the first prong than the second prong, the at least one localized reduction in cross-sectional area changing the flow of gases downstream of the at least one localized reduction in cross-sectional area.

* * * * *